(12) United States Patent
Sherley et al.

(10) Patent No.: US 7,883,891 B2
(45) Date of Patent: Feb. 8, 2011

(54) UNIQUE PROPERTIES OF STEM CELLS

(75) Inventors: James L Sherley, Boston, MA (US); Joshua R. Merok, Chicago, IL (US)

(73) Assignee: Massachusetts Institute of Technology, Cambridge, MA (US)

( * ) Notice: Subject to any disclaimer, the term of this patent is extended or adjusted under 35 U.S.C. 154(b) by 1244 days.

(21) Appl. No.: 10/483,601

(22) PCT Filed: Jul. 17, 2002

(86) PCT No.: PCT/US02/22573

§ 371 (c)(1), (2), (4) Date: May 13, 2004

(87) PCT Pub. No.: WO03/029402

PCT Pub. Date: Apr. 10, 2003

(65) Prior Publication Data

US 2005/0074874 A1   Apr. 7, 2005

Related U.S. Application Data

(60) Provisional application No. 60/306,072, filed on Jul. 17, 2001.

(51) Int. Cl.
*C12N 5/08*   (2006.01)
(52) U.S. Cl. .................................................... 435/366
(58) Field of Classification Search .................. None
See application file for complete search history.

(56) References Cited

U.S. PATENT DOCUMENTS

2003/0133918 A1   7/2003   Sherley

FOREIGN PATENT DOCUMENTS

WO   WO 02/090992 A2   11/2002

OTHER PUBLICATIONS

Arianne Heinrichs (Nature Reviews, Molecular Cell Biology. Nov. 2007; vol. 8, p. 851).*
Kiel et al. (Nature. Sep. 13, 2007; 449: 238-244).*
Smith (Development. Dec. 2004; 132: 681-687).*
Potten et al. (Journal of Cell Science. Mar. 2002; 115: 2381-2388).*
Shinin et al. (Nature Cell Biology. Jul. 2006; 8(7): 677-687 and S1-S5).*
Conboy et al. (PLoS Biology. May 2007; 5(5)e102: 1120-1126).*
Karpowicz et al. (Journal of Cell Biology. 2005; 170(5): 721-732).*
Sherley et al. (MIT Ref. No. 9273, NP Ref. No. 800953-051562).*
Rando (Cell 129, Jun. 29, 2007; 1239-1243).*
Lansdorp (Cell 129, Jun. 29, 2007; 1244-1247).*
Yan et al. (Stem Cell Rev. 2007; 3: 265-269).*
Waghmare et al. (EMBO. 2008; 27: 1309-1320).*
Fei et al. (Cerebral Cortex. 2009; 19 (supplement 1): i49-i54).*
Falconer et al. (Nature, Jan. 7, 2010; 463: 93-98).*
Moore et al. ("Hematopoietic Stem Cells", Regulatory Networks in Stem Cells. Stem Cell Biology and Regenerative Medicine, Humana Press 2009, part IV; pp. 347-377).*
Cairns, John; PNAS; 99(16):10567-10570 (Aug. 6, 2002).
Merok, Joshua R. et al.; Journal of Biomedicine and Biotechnology; 1(1):25-27 (2001).
Merok, Joshua R. et al.; Cancer Research; 62:6791-6795 (Dec. 1, 2002).
Tannenbaum, Emmanuel et al.; Physical Review E; 71:041914-1 through 041914-9 (2005).

* cited by examiner

*Primary Examiner*—Scott Long
(74) *Attorney, Agent, or Firm*—Nixon Peabody, LLP

(57) ABSTRACT

The present invention is directed to unique properties of stem cells, including methods to identify stem cell markers by identifying molecules associated specifically with chromosomes in stem cells. More particularly, we have discovered that somatic stem cells repeatedly inherit an entire complement of chromosomes that contain the same parental template DNA strands from one generation to the next. The present invention also provides methods related to diagnosis, prognosis, and treatments for cancer and aging in mammalian tissus, including human.

16 Claims, 6 Drawing Sheets

UNIQUE PROPERTIES OF STEM CELLS

CROSS-REFERENCE TO RELATED APPLICATIONS

This application is a 371 National Phase Entry Application of co-pending International Application PCT/US02/22573, filed 17 Jul. 2002 which designated the U.S. and which claims the benefit under 35 U.S.C. §119(e) of U.S. Provisional Application 60/306,072, filed 17 Jul. 2001.

This invention was supported by Defense Advanced Research Projects Agency grant N0014-98-1-0760 and the government of the United States has certain rights thereto.

FIELD OF THE INVENTION

The present application is directed to the use of the nucleic acid in stem cells, including methods to identify stem cell specific chromosomes, stem cell specific markers, methods to identify and enumerate stem cells, as well as methods of using such nucleic acids, preferably in connection with cellular aging and transplantation.

BACKGROUND OF THE INVENTION

Considerable attention has focused on stem cells and their uses in a range of therapies. The availability of somatic stem cells from adult tissues would greatly contribute to cell replacement therapies such as bone marrow transplants, gene therapies, tissue engineering, and in vitro organogenesis. Production of autologous stem cells to replace injured tissue would also reduce the need for immune suppression interventions.

Somatic stem cells, also known as adult stem cells, are stem cells derived from adult tissues, in contrast to other sources of stem cells such as cord stem cells and embryonic stem cells, which may originate from a variety of sources of embryonic tissue. Somatic stem cells are particularly attractive for a range of therapies in light of the ongoing controversies surrounding the use of embryonic stem cells.

Somatic stem cells possess the ability to renew adult tissues (Fuchs and Segre, 2000). Cell growth is a carefully regulated process that responds to the specific needs of the body in different tissues and at different stages of development. In a young animal, cell multiplication exceeds cell loss and the animal increases in size; in an adult, the processes of cell division and cell loss are balanced to maintain a steady state. For some adult cell types, renewal is rapid: intestinal cells and certain white blood cells have a half-life of a few days before they die and are replaced. In contrast, the half-life of human red blood cells is approximately 100 days; healthy liver cells rarely die, and in adults, there is a slow loss of brain cells with little or no replacement.

Somatic stem cells may also play an important role during aging. As an animal ages, cellular changes that occur in tissues are also likely to reflect alterations in the number and function of somatic stem cells. One model which has been proposed is that alterations in a cell's DNA reflects the relative age of the cell. These alterations could include stable covalent base modification (e.g., methylation) or poorly repaired forms of oxidative and other chemical damage (production of hypoxanthine and xanthine bases via deamination), as well as base pair errors introduced during replication. Accumulation of these defects over time would eventually lead to declines in stem cell number and function to the ultimate demise of tissue function and life. Thus, it would be desirable if there was a way to counter some of the aforementioned effects of aging to rejuvenate aged tissues.

Beyond their potential therapeutic applications, homogenous preparations of somatic stem cells would have another important benefit, the ability to study their molecular and biochemical properties. The existence of stem cells in somatic tissues is well established by functional tissue cell transplantation assays (Reisner et al, 1978). However, their individual identification has been difficult to accomplish. Even though their numbers have been enriched by methods such as immuno-selection with specific antibodies, there are no known markers that uniquely identify stem cells in somatic tissues (Merok and Sherley, 2001). Secondly, somatic stem cells are often present in only minute quantities, are difficult to isolate and purify, and their numbers may decrease with age. For example, brain cells from adults that may be neuronal stem cells have only been obtained by removing a portion of the brain of epileptics, not a trivial procedure.

Thus, there is a need to develop simple and reliable methods for the identification of stem cell-specific markers for the development of stem cell-specific molecular probes. Such stem cell markers could then be used to develop methods to identify stem cells in tissues and to isolate them directly from tissues. The ability to readily obtain stem cells in human tissues would permit easy harvesting of those cells as well as add greatly to our understanding of tissue cell physiology. An understanding of the mechanisms which control stem cell number can suggest new therapeutic strategies for cancer prevention and treatment, and for reducing morbidity associated with aging.

Accordingly, methods to isolate and expand stem cells from somatic tissue, particularly without significant differentiation, are highly desirable.

Attempts at isolating somatic stem cells have encountered a number of significant difficulties. Attempts at somatic stem cell isolation have been described, for example, in studies to enrich for hematopoietic stem cells (HSCs; Phillips et al., 2000). However, although high degrees of enrichment have been reported, so far HSCs (and other somatic stem cells) have neither been identified nor purified to homogeneity. A major obstacle to these two challenges is the lack of stem cell-specific molecular probes.

Thus, despite the need for methods to isolate somatic cells from an individual, it has not been possible to readily do so. Accordingly, it would be desirable to have a method to identify markers associated with somatic stem cells in mammalian tissues. It would also be desirable to have methods to detect aging in mammalian tissues, including humans. Finally, it would be desirable to have methods to reduce or reverse at least some of the consequences of such aging in adult mammalian tissues, including humans.

SUMMARY OF THE INVENTION

We have now discovered methods for identifying stem cell chromosomes, by exposing cells undergoing cell cycle division to a detectable nucleotide analogue, and identifying those chromosomes which do not incorporate the nucleotide analogue. Preferably, the nucleotide analogue is 5-bromodeoxyuridine.

In a preferred embodiment, mitotic cells are isolated using mitotic shake-off after exposing the cells to the nucleotide analogue labeling regimens to enrich for cells undergoing cell cycle division. In a further preferred embodiment, cytochalasin D is used to generate bi-nucleated single cells to improve detection of stem cell chromosomes.

The invention also provides methods to identify stem cells markers by identifying molecules associated specifically with chromosomes in stem cells; identification of markers that are specific to such stem cells permit the development of stem cell-specific molecular probes.

The stem cell markers of the present invention are associated with alterations of the stem cell chromosomes compared to non-stem cell chromosomes. For example, stem cell chromosomes may have specific molecules, such as proteins, RNA, or DNA, associated with them. Alternatively, the chromosomes of stem cells may have characteristic alterations, such as modifications (including methylation, deamination, glycosylation, acetylation, phosphorylation, lipidation, and previously unknown modifications) or specific structural conformities (including regions of single-stranded DNA).

In a preferred embodiment, the stem cell marker is an antibody which specifically recognizes stem cell chromosomes. The present invention also provides methods to generate such antibodies, by isolating stem cell chromosomes and using hybridoma technology to raise monoclonal antibodies against them. An alternative approach is to identify protein(s) uniquely associated with stem cell chromosomes using 2-D gel analysis, and raise anti-peptide antibodies to those proteins. A third approach is to identify stem cell chromosome-specific genes using microarray analysis, and to raise anti-peptide antibodies to the proteins they encode.

The present invention also provides a method for isolating stem cells, using for example, a means to identify the unique stem cell chromosome such as a stem cell chromosome specific antibody, with flow cytometry to separate stem cells from non-stem cells.

The present invention also provides methods for detecting stem cells in a biological sample. In one embodiment, cells undergoing cell cycle division are exposed to a detectable nucleotide analogue, and stem cells are identified as those cells containing chromosomes which do not incorporate the nucleotide analogue. Preferably, the nucleotide analogue is 5-bromo-deoxyuridine (BrdU), which is detected using a fluorescent anti-BrdU antibody or quenching of bound fluorescent Hoechst DNA dyes. Methods for detecting stem cells also include the use of the stem cell markers described above, and any method which allows their detection. For example, immunohistochemistry with the stem cell antibody. In a further preferred embodiment, image-programmed laser scanning cytometry is used to detect fluorescently labeled cells. In yet another preferred embodiment, flow cytometry may be used to detect binucleated cells that contain one labeled and one unlabeled nucleus.

The use of the stem cell markers permits one to enumerate the number of stem cells in an animal.

A method to rejuvenate aged tissue can be accomplished by replacing the immortal DNA strand in somatic stem cells, for example by inducing their replication to eliminate stem cells of age-dependent genomic defects.

In one preferred embodiment, stem cells can be harvested from an animal, expanded by symmetric replication, cryopreserved and thawed, expanded and administered to the animal to replace the age-damaged stem cells at later stages in the life cycle.

Another preferred embodiment provides a method of prognosis or diagnosis, for example of aging, by comparing the number and quality (e.g., functional immortal strand co-segregation efficiency) of somatic stem cells in a patient or tissue to a control.

Another preferred embodiment provides a method of predicting bone marrow transplant engraftment success by enumerating the number and quality and quality of hematopoietic stem cells present in the transplanted sample, by removing a prognostic fraction of the bone marrow sample prior to transplantation, and estimating the number of stem cells in the transplanted sample by enumerating the number of stem cells present in the prognostic fraction.

BRIEF DESCRIPTION OF THE DRAWINGS

In FIG. 1A, chromosomes are selectively co-segregated into the next-generation SSC. In FIG. 1B, if SSCs underwent the usual form of mitotic segregation, characterized by independent chromosome segregation, all chromosomes would assort with equal frequency to either SSCs and their differentiating sisters (square). If independent segregation occurred in SSCs, mutations that arose from errors during the synthesis of new strands would have a 50% probability of remaining in the SSC genome. Immortal strand co-segregation would insure that all such mutations were always segregated to the non-SSC sister.

FIG. 2A, FIG. 2C) or p53-inducible cells induced to cycle with asymmetric cell kinetics one cell generation (GT) earlier (Ind-8; FIG. 2B, FIG. 2D) were cultured with BrdU for 0.75 GT (FIGS. 2A-2B) or 2.4 GT (FIGS. 2C-D). Solid lines with open circles, relative DNA content determined by fluorescent dye binding; Dotted lines, 3H-labeled BrdU-free internal DNA strandard. Symbols above graphs denote cell kinetics with respect to predicted BrdU content: Circle, cycling cell. Square, non-cycling cell. Open, cell with unlabeled chromosomes (LL, light-light DNA). Half-closed, cell with hemi-substituted chromosomes (HL, heavy-light DNA). Closed, cell with bi-substituted chromosomes (HH, heavy-heavy DNA). Color-faded, cell with equivalent numbers of HH and HL chromosomes. In FIG. 2C, the outcome for random chromosome segregation by exponentially cycling cells is shown. Equivalent numbers of HH and HL chromosomes segregate to sister cells (Color-faded circles). In FIG. 2D, the outcome of immortal strand co-segregation by asymmetrically cycling cells is depicted. The non-cycling sisters (closed square) receive only bi-substitued HH chromosomes, whereas the cycling stem cell-like sisters (half-closed circle) co-segregates only hemi-substituted HL chromosomes that contain unsubstituted immortal DNA strands.

FIG. 3A shows a phase contrast image. FIG. 3B shows Hoechst DNA staining to detect binucleates. FIG. 3C shows anti-BrdU immunofluorescence. The cell with lower anti-BrdU fluorescence is predicted to contain co-segregated chromosomes with immortal unsubstituted template DNA strands.

FIG. 4A, cells cultured without BrdU; FIGS. 4B-4C, cells dividing with the indicated kinetics cultured in the continuous presence of BrdU for 144 hours (approximately 6 PDCs). FIG. 4B is the average result of two independent experiments with median fluorescence intensities per area of 127 and 121. Both were significantly different than the value of 116 obtained for cells cycling with exponential kinetics ($p<0.0001$ and $p=00.0023$, respectively). The average number of chromosomes analyzed was 535.

FIGS. 5E-5G are examples of binucleates with asymmetric anti-BrdU fluorescence at high power showing linear arrays of corresponding phase contrast, DAPI fluorescence, and anti-BrdU fluorescence images. FIGS. 5H-5J, overlays of DAPI fluorescence and anti-BrdU fluorescence for FIGS. 5E-5G, respectively.

DETAILED DESCRIPTION OF THE INVENTION

Figure 1:
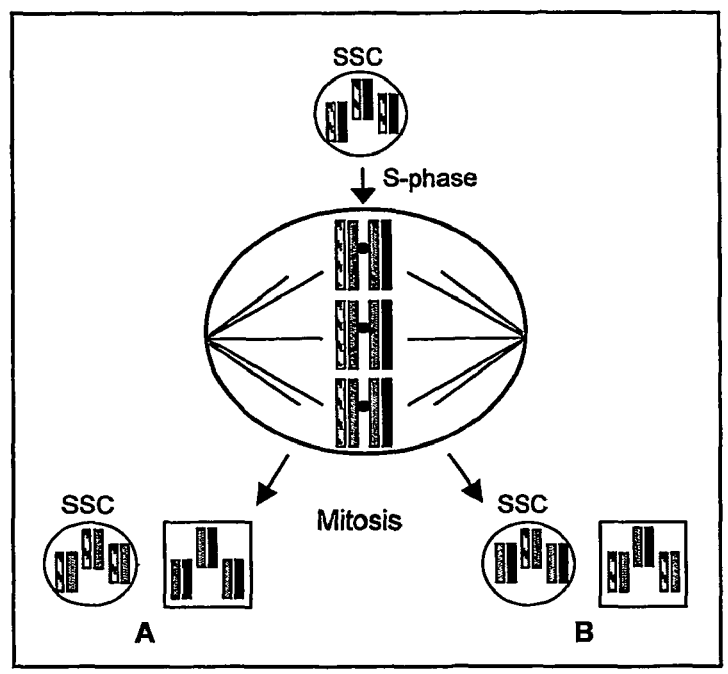
FIGS. 1A-B depict the chromosome co-segregation predicted by the immortal strand hypothesis (ISH). Paired bold lines indicate individual DNA strands of chromosomes in cell nuclei. After semi-conservative DNA replication, each immortal DNA strand (bold red-striped lines) is paired with a newly synthesized DNA strand (gray bold lines). The ISH states that somatic stem cells (SSC) continuously retain the set of chromosomes (40 in mice, 46 in humans) that contains old parental DNA strands.

We have now discovered methods for identifying stem cell chromosomes, by exposing cells undergoing cell cycle division to a detectable nucleotide analogue, and identifying those chromosomes which do not incorporate the nucleotide analogue. We have also discovered methods to identify stem cells markers, by identifying molecules associated specifically with the chromosomes that do not incorporate the nucleotide analogue. These markers can be used to rapidly identify stem cells. More particularly, we have discovered direct evidence for the hypothesis that somatic stem cells repeatedly inherit an entire complement of chromosomes that contain the same parental template DNA strands from one generation to the next.

Thus, methods to identify molecules specifically associated with the immortal strand in stem cells are possible. The present invention further provides methods to counter aging in an animal, by replacing the aged immortal DNA strand in somatic stem cells. One approach is to take advantage of the fact that the majority of the non-replicative changes that occur in the aging cell's nucleic acids are not fixed and thus can be eliminated by inducing the replication on the immortal strand. Thus, one eliminates the somatic stem cells of age-dependent, environmentally induced and endogenous genomic defects. Another method is to identify and extract somatic stem cells from an individual early in their lifespan, preferably from a range of the tissues in which they are present, expand such populations of cells and then cryopreserve them. The in vivo stem cells can be monitored to determine aging effects and when such effects are identified, some of the appropriate somatic stem cells can be thawed, expanded and administered to replace the aging cells. One can also compare genomic differences between stem cells and a control, such as non-stem cells to identify differences that arise due to errors in DNA replication in the normal cells, which are not present in the stem cells. These can be used to identify associations with particular disease states. One can also use a control which is based upon a standard stem cell or the individual's own stem cells from an earlier stage in life to identify changes.

Over a quarter of a century ago, the hypothesis was put forth that an immortal DNA strand mechanism functioned in somatic stem cells that divide with asymmetric cell kinetics (Cairns, 1975). The immortal strand hypothesis (ISH) states that somatic stem cells repeatedly inherit an entire complement of chromosomes that contain the same parental template DNA strands from one generation to the next. The DNA strands that are preferentially retained by adult stem cells are called "immortal" DNA strands, because they are predicted to persist within long-lived adult stem cells for the entire life span of mammals (Cairns, 1975; Marshman et al., *BioEssays* 24:91-98 (2002); Potten et al., *J. Cell Sci.* 115: 2381-8 (2002)). This coordinated, non-random, pattern of mitotic chromosome segregation was proposed as an essential protective mechanism against the development of neoplasia. Selective retention of immortal DNA templates would allow somatic stem cells to avoid fixation of carcinogenic spontaneous gene mutations that arise from DNA replication errors. Our development of cultured somatic cells that divide with asymmetric stem cell kinetics (Sherley et al., 1995a; Sherley et al., 1995b; Rambhatla et al., 2001) allowed a direct test of the ISH. The present invention demonstrates selective co-segregation of chromosomes containing immortal template DNA strands by cells that cycle with asymmetric kinetics.

The predominant way somatic stem cells divide is by asymmetric cell kinetics (see FIG. 1). During asymmetric kinetics, one daughter cell divides with the same kinetics as its stem cell parent, while the second daughter gives rise to a differentiating non-dividing cell lineage. The second daughter may differentiate immediately; or, depending on the tissue, it may undergo a finite number of successive symmetric divisions to give rise to a larger pool of differentiating cells. In tissues with high rates of cell turnover, the endpoint for differentiated terminal cells is programmed cell death by apoptosis. Thus, the asymmetric cell kinetics characteristic of somatic stem cells play a central role in their ability to renew adult tissues.

Prior to our work, several groups have reported indirect evidence for the existence of immortal DNA strand co-segregation in adult mammalian tissues in vivo. The essence of this evidence is the detection of cells that appear either to release incorporated $^3$H-thymidine more rapidly than would be expected for random chromosome assortment, or retain the label for extended periods of time.[8-11] Even earlier in vitro studies reported evidence for unequal segregation of labeled mitotic chromosomes in diverse species including cultured murine embryonic fibroblasts and plant meristem cells.[12,13] With the model cells employed in our studies, we now define parental DNA template co-segregation as a specific property of cells that divide with asymmetric kinetics.

Somatic stem cells provide a model for studying fundamental molecular and cellular processes important in aging and age-related diseases. For example, during aging, they can be used to study how the expression of the telomerase gene gets turned off during differentiation, which has critical importance for understanding both aging and cancer. Additional studies can be used to define the factors that control the self-renewal capacity of pluripotent stem cells or the differentiation of pluripotent stem cells into various cell types when grown in cell culture or when transplanted into human tissue. Other assays can be used to identify those factors leading to optimum therapeutic benefit, including the best type of cells for transplantation and what happens when cells are transplanted into hosts of different ages or into hosts with different diseases. Such assays can result in improvements in cell transplantation and tissue regeneration therapies in age-related disorders.

Method of Identifying Stem Cells and Stem Cell Chromosomes

We have now discovered methods for identifying stem cell chromosomes by exposing a population of cells undergoing cell cycle division to a detectable nucleotide analogue, and identifying those chromosomes which do not incorporate the detectable nucleotide analogue. This method also identifies stem cells, as those cells containing the stem cell chromosomes. As used herein, "chromosome" refers the linear arrangement of DNA including genes and non-coding sequences, as well as other associated nucleic acid(s) (including additional DNAs and RNAs), proteins and other molecules, which together represent the nuclear inherited genetic material of a cell.

Figure 6:
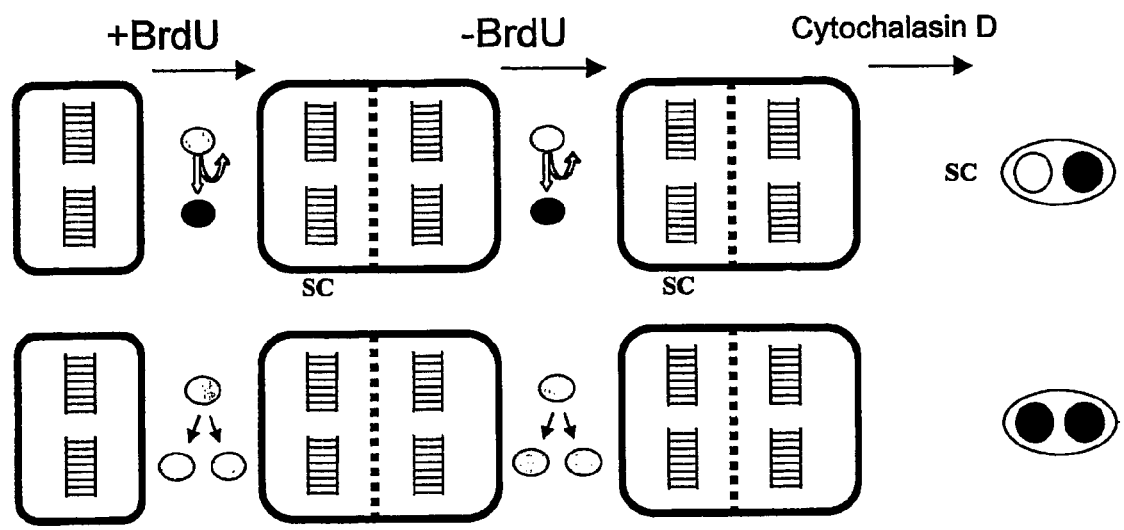
FIG. 6 depicts an assay to detect adult stem cells (SC) based on their unique immortal DNA strand co-segregation function. The light strands represent the immortal DNA strand; the dark strands represent non-immortal DNA strand labeled with synthetically incorporated bromodeoxyuridine (BrdU); and the dashed strands represent non-immortal unlabeled DNA strand. Dotted lines indicate division plane at anaphase of mitosis of either the preceding single cell or the preceding left daughter cell. The top row indicates the assay result expected for asymmetrically dividing adult stem cells that co-segregate chromosomes with immortal DNA strands. The bottom row indicates the assay result expected for cells with symmetric cell kinetics and no immortal DNA strand mechanism.

The method of the present invention for detecting stem cells, containing stem cell chromosomes, comprises a four step assay. The first step of the assay is a labeling step, in which a cell preparation of interest is cultured for approximately one generation in the presence of a detectable nucleotide analogue such as 5-bromodeoxyuridine (BrdU). The second step of the assay is a chase step, in which the detectable nucleotide analogue is washed out and the cells are grown for an additional generation. In the third step of the assay, the cell preparation is treated allow identification and comparison of two sister nuclei, derived from a single parent nucleus. For example, cytochalasin D can be added for an additional generation, to allow the accumulation of binucleated cells by preventing cytokinesis and trapping post-mitotic sister nuclei within a single cell. In the fourth step of the assay, the cell preparation is analyzed to detect the distribution of the nucleotide analogue in binucleated cells. Binucleated cells which contain one labeled nucleus, which has incorporated the nucleotide analogue, and one unlabeled nucleus, which has not incorporated the nucleotide analogue, are stem cells, in which the immortal DNA strands have co-segregated to the unlabeled nucleus, which is thus also identifiable as the nucleus containing stem cell chromosomes. This assay is depicted in FIG. 6.

As used herein, a "generation" refers to the duration of time necessary for a cell to undergo one complete cell cycle, including nuclear and cellular division. The length of a generation is cell-type specific, and can be determined empirically using techniques well known in the art. For example, many cycling mammalian cells typically divide every 16-24 hours. The duration of the generation may be optimized for each cell type for use with this assay.

Preferably, the nucleotide analogue is any nucleotide base analogue which can be incorporated into replicating cellular DNA. Preferred nucleotide analogues include 5-bromodeoxyuridine (BrdU), $^3$H-thymidine, halogenated nucleotide base analogues such as iodo-uridine, and nucleotide analogues which can be incorporated into replicating cellular DNA following permeabilization of the plasma membrane. More preferably, the nucleotide analogue is BrdU or $^3$H-thymidine.

Even more preferably, the detectable nucleotide analogue used in the first step of the assay, the labeling step, is BrdU. BrdU can be used at any concentration which allows its incorporation into replicating DNA without interfering with cellular function. For example, BrdU may be used at 5-20 µM.

During the chase step of the assay, the detectable nucleotide analogue is washed out of the cell culture medium. When BrdU is used, BrdU-free medium supplemented with thymidine can be used to limit further incorporation of BrdU. Thymidine can be used for example at a concentration 5-fold higher than that of the BrdU used during the labeling step.

During the third step of the assay, any method which allows identification and comparison of two sister nuclei, derived from a single parent nucleus, can be used, including all agents and methods that block mitosis at any stage. Preferred examples include but are not limited to cytochalasin D, colcemid, colchicine, mitotic shake off (described further below), nocodazole, cell synchronization, expression of specific mitotic arrest genes, repression of specific mitotic promoting genes, and other techniques known in the art.

One preferred method which allows identification and comparison of two sister nuclei, derived from a single parent nucleus, is the use of cytochalasin D in the culture medium to capture cells as bi-nucleated cells, which contain two post-mitotic sister nuclei captured in a single cell. This method enhances the detection of co-segregation of the unlabeled DNA strands. Cytochalasin D can be used at any concentration which disrupts cell but not nuclear division; the concentration of cytochalasin D depends on the tissue and/or cell type. Preferably, 2 µM cytochalasin D is used.

In the final step of the assay, labeled chromosomes can be detected by any means known in the art. For example, if BrdU has been used as the detectable nucleotide analogue, anti-BrdU immunofluorescence can be used. Other detection systems include the BrdU-induced fluorescence quenching of the DNA-binding dyes Hoechst 33258 and Hoechst 33342, as well as the CyQUANT Cell Proliferation Assay Kit (available from Molecular Probes Inc.). Fluorescent labeling can be quantitated using digital fluorescence imaging, flow cytometry, or image-programmed laser scanning cytometry.

In a preferred embodiment, mitotic cells can isolated prior to exposing cells to a detectable nucleotide analogue. Isolating mitotic cells prior to the labeling step decreases the background by eliminating non-dividing cells, since the method requires cells undergoing cell cycle division. One preferred method for isolating mitotic cells is the mitotic shake-off method, in which mitotic cells are isolated every 60 minutes by shaking cell cultures to loosen cells undergoing mitosis, which releases the mitotic cells into the culture medium, and collecting the culture medium to isolate the mitotic cells. Preferably, the cells isolated in the first two collections are discarded. The mitotic shake-off method can be used over several hours, with the individual collections of mitotic cells pooled and stored on ice prior to beginning the exposure to the nucleotide analogue. Preferable, mitotic cells are collected for 20 hours. Such cells are typically over 95% viable, as determined using trypan blue analysis.

Applications of Methods to Identify and Enumerate Stem Cells

The present invention provides methods for identifying both stem cells and stem cell chromosomes. These methods are useful for a wide range of applications, including but not limited to the following examples.

Methods for identifying stem cells are useful for isolating purified populations of stem cells. For example, flow cytometry can be used to separate binucleate cells with one labeled and one unlabeled nucleus from binucleated cells with even distribution of the labeled nucleotide analogue. Purified populations of stem cells are useful for a wide range of applications, including basic research investigations as well as potential therapeutic uses such as gene therapy, tissue engineering, and cell therapy.

The methods of the present inventions can also be used to identify adult stem cells derived from embryonic stem cells. Embryonic cells are not ideal sources of stem cells for cell therapy because of their tumor-forming properties. Instead, the methods of the present invention can be used to identify adult stem cells derived from instructed differentiation of embryonic stem cells. Adult stem cells, with asymmetric cell kinetics and intact immortal strand mechanisms, can provide a preferable acceptable level of tumorigenic risk.

The methods of the present inventions can also be used to quantify alterations in stem cell number and function as pre-neoplastic indicators.

The methods of the present inventions can also be used as a metric for developing quality control criteria and standard operating procedures for the stem cell production industry.

The methods of the present inventions can also be used to develop toxicity and drug discovery screens for compounds that alter stem cell function.

Somatic Stem Cells

As used herein, somatic stem cells derived from adult tissues are sometimes referred to as somatic tissue stem cells or somatic stem cells or simply as stem cells.

Any source of somatic stem cells can be used in the methods of the present invention, including primary stem cells from an animal as well as model cell lines which exhibit asymmetric cell kinetics which characterize somatic stem cells.

One regulator of asymmetric cell kinetics is the p53 tumor suppressor protein. Several stable cultured murine cell lines have been derived that exhibit asymmetric cell kinetics in response to controlled expression of the wild-type murine p53 (FIG. 1B). (Sherley, 1991; Sherley et al, 1995 A-B; Liu et al., 1998 A-B; Rambhatla et al., 2001).

The p53 model cell lines have been used to define cellular mechanisms that regulate asymmetric cell kinetics. The methods of the present invention can use these p53 model cells lines, as well as other cell lines which exhibit conditional asymmetric cell kinetics. The cell lines can be cultured using any conditions known in the art, and described further below.

Somatic stem cells of the present invention include any stem cells isolated from adult tissue. Somatic stem cells include but are not limited to bone marrow derived stem cells, adipose derived stem cells, mesenchymal stem cells, neural stem cells, liver stem cells, and pancreatic stem cells. Bone marrow derived stem cells refers to all stem cells derived from bone marrow; these include but are not limited to mesenchymal stem cells, bone marrow stromal cells, and hematopoietic stem cells. Bone marrow stem cells are also known as mesenchymal stem cells or bone marrow stromal stem cells, or simply stromal cells or stem cells.

The stem cells act as precursor cells, which produce daughter cells that mature into differentiated cells. In some embodiments, somatic tissue stem cells can be isolated from fresh bone marrow or adipose tissue by fractionation using fluorescence activated call sorting (FACS) with unique cell surface antigens to isolate specific subtypes of stem cells (such as bone marrow or adipose derived stem cells).

Two preferred embodiments provide bone marrow or adipose tissue derived stem cells, which may be obtained by removing bone marrow cells or fat cells, from a donor, either self or matched, and placing the cells in a sterile container. If the cells are adherent cells, the sterile container may include a plastic surface or other appropriate surface to which the cells adhere. For example, stromal cells will adhere to a plastic surface within 30 minutes to about 6 hours. After at least 30 minutes, preferably about four hours, the non-adhered cells may be removed and discarded. The adhered cells are stem cells, which are initially non-dividing. After about 2-4 days however the cells begin to proliferate.

Cells can be obtained from donor tissue by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument. Dissociation of cells can be carried out in any acceptable medium, including tissue culture medium. For example, a preferred medium for the dissociation of neural stem cells is low calcium artificial cerebrospinal fluid.

The dissociated stem cells or model cell lines can be cultured in any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds which enhance guanine nucleotide biosynthesis, although generally at levels below the effective concentration to suppress asymmetric cell kinetics. Thus, preferably a defined, serum-free culture medium is used, as serum contains unknown components (i.e. is undefined). Preferably, if serum is used, it has been dialyzed to remove guanine ribonucleotide precursors (rGNPrs). A defined culture medium is also preferred if the cells are to be used for transplantation purposes. A particularly preferable culture medium is a defined culture medium comprising a mixture of DMEM, F12, and a defined hormone and salt mixture.

The culture medium can be supplemented with a proliferation-inducing growth factor(s). As used herein, the term "growth factor" refers to a protein, peptide or other molecule having a growth, proliferative, differentiative, or trophic effect on neural stem cells and/or neural stem cell progeny. Growth factors that may be used include any trophic factor that allows stem cells to proliferate, including any molecule that binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGF.alpha.), and combinations thereof.

Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGF.bets), insulin-like growth factor (IGF.sub.-1) and the like.

Stem cells can be cultured in suspension or on a fixed substrate. One particularly preferred substrate is a hydrogel, such as a peptide hydrogel, as described below. However, certain substrates tend to induce differentiation of certain stem cells. Thus, suspension cultures are preferable for such stem cell populations. Cell suspensions can be seeded in any receptacle capable of sustaining cells, particularly culture flasks, cultures plates, or roller bottles, more particularly in small culture flasks such as 25 $cm^2$ cultures flasks. In one preferred embodiment, cells are cultured at high cell density to promote the suppression of asymmetric cell kinetics.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30.degree. C. to 40.degree. C. Cells are preferably cultured at temperatures between about 32.degree. C. to about 38.degree. C., and more preferably between about 35.degree. C. to about 37.degree. C.

Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Biochemical Methods to Isolate Proteins Specifically Associated with the Immortal Strand A variety of biochemical methods can be used to isolate proteins specifically associated with the immortal strand in somatic stem cells. For example, one can use standard biochemical techniques to isolate proteins or nucleic acids associated with chromosomes from somatic stem cells. Such an isolate can then be used to identify molecules associated specifically with the immortal strand, for example by using protein fractionation techniques to identify proteins present in such an isolate, or by generating antibodies to the preparation, and screening the resulting antibodies for those which specifically recognize immortal strands.

Antibodies

The term "antibodies" is meant to include monoclonal antibodies, polyclonal antibodies and antibodies prepared by recombinant nucleic acid techniques that are selectively reactive with polypeptides encoded by nucleotide sequences of the present invention. The term "selectively reactive" refers to those antibodies that react with one or more antigenic determinants e.g. on the immortal strand and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block binding interactions.

For preparation of antibodies directed toward the protein preparation isolated from the immortal strand, any technique that provides for the production of antibody molecules may be used.

Antigenic material for raising antibodies which recognize stem cell chromosomes can be prepared by isolating stem cell chromosomes using the methods described above. For example, mitotic chromosomes that contain immortal DNA strands can be isolated by fluorescence-activated cell sorting (FACS). The same principles that apply to detection of immortal DNA strands in situ can be applied to their isolation by FACS. For example, cells can be fluorescently labeled to distinguish stem cell chromosomes from non-stem cell chromosomes, and flow cytometry can be used to isolate the non-labeled stem cell chromosomes; this material can be used to generate monoclonal or polyclonal antibodies using techniques well-known in the art, including hybridoma technology.

For example, mice can be immunized twice intraperitoneally with approximately 50 micrograms of immunogen per mouse. Sera from such immunized mice can be tested for antibody activity by immunohistology or immunocytology on any host system expressing such polypeptide or by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymed Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

Another method for preparing antibodies is by using hybridoma mRNA or splenic mRNA as a template for PCT amplification of such genes [Huse, et al., *Science* 246:1276 (1989)]. For example, intrabodies can be derived from murine monoclonal hybridomas [Richardson, J. H., et al., *Biochem and Biophys Res Comm.* 197: 422-427 (1993); Muashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines [Marasco, W. A., et al., *Proc. Natl. Acad. Sci. USA* 90:7889-7893 (1993); Chen, S. Y., et al., *Proc. Natl. Acad. Sci. USA* 91:5932-5936 (1994)]. Another example includes the use of antibody phage display technology to construct new antibodies against different epitopes on a target molecule [Burton, D. R., et al., *Proc. Natl. Acad. Sci. USA* 88:10134-1-137 (1991); Hoogenboom, H. R., et al., *Immunol. Rev.* 130:41-68 (1992); Winter, G., et al., *Ann. Rec. Immunol.* 12:433-355 (1994); Marks, J. D., et al., *J. Biol. Chem.* 267:16007-16010 (1992); Nissim, A., et al., *EMBO J.* 13:692-698 (1994); Vaughan, T. J., et al., *Nature Bio.* 14:309-314 (1996); Marks, C., et al., *New Eng. J. Med.* 335: 730-733 (1996)]. For example, very large naive human sFV libraries have been and can be created to offer a large source of rearranged antibody genes against a plethora of target molecules. Smaller libraries can be constructed from individuals with autoimmune disorders [Portolano, S,. et al., *J. Immunol.* 151:2839-2851 (1993); Barbas, S. M., et al., *Proc. Natl. Acad. Sci. USA* 92:2529-2533 (1995)] or infectious diseases [Barbas, C. F., et al., *Proc. Natl. Acad. Sci.*

USA 89:9339-9343 (1992); Zebedee, S. L., et al., *Proc. Natl. Acad. Sci. USA* 89:3175-3179 (1992)] in order to isolate disease specific antibodies.

Other sources include transgenic mice that contain a human immunoglobulin locus instead of the corresponding mouse locus as well as stable hybridomas that secrete human antigen-specific antibodies [Lonberg, N., et al., *Nature* 368: 856-859 (1994); Green, L. L., et al., *Nat. Genet.* 7:13-21 (1994)]. Such transgenic animals provide another source of human antibody genes through either conventional hybridoma technology or in combination with phage display technology. In vitro procedures to manipulate the affinity and find specificity of the antigen binding site have been reported including repertoire cloning [Clackson, T., et al., *Nature* 352: 624-628); marks, J. D., et al., *J. Mol. Biol.* 222: 581-597 (1991); Griffiths, A. D., et al., *EMBO J.* 12: 725-734 (1993)], in vitro affinity maturation [Marks, J. D., et al., *Biotech* 10: 779-783 (1992); Gram, H., et al., *Proc. Natl. Acad. Sci. USA* 89: 3576-3580 (1992)], semi-synthetic libraries [Hoogenboom, H. R., supra; Barbas, C. F., supra; Akamatsu, Y., et al., *J. Immunol.* 151: 4631-4659 (1993)] and guided selection [Jespers, L. S. et al., *Bio Tech* 12: 899-902 (1994)]. Starting materials for these recombinant DNA based strategies include RNA from mouse spleens [Clackson, t., supra] and human peripheral blood lymphocytes [Portolano, S., et al., supra; Barbas, C. F., et al., supra; Marks, J. D., et al., supra; Barbas, C. F., et al., *Proc. Natl. Acad. Sci. USA* 88: 7978-7982 (1991)] and lymphoid organs and bone marrow from HIV-1-infected donors [Burton, D. R., et al., supra; Barbas, C. F., et al., *Proc. Natl. Acad. Sci. USA* 89:9339-9343 (1992)].

For preparation of monoclonal antibodies directed toward the proteins isolated from the immortal strands, any technique that provides for the production of antibody molecules by continuous cell lines may be used. For example, the hybridoma technique originally developed by Kohler and Milstein (*Nature,* 256: 495-7,1973), as well as the trioma technique, the human B-cell hybridoma technique (Kozbor et al., *Immunology Today* 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al., U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Another approach for generating antibodies uses 2-dimensional gel analyses to identify proteins that are only extracted from immortal strand-containing chromosomes. The identities of such proteins can be established by micro-sequencing and protein bioinformatics. Anti-peptide antibodies can then be raised against proteins identified by this method and evaluated for specific reactivity against immortal strand-containing chromosomes.

Another approach for generating antibodies uses gene micro-array analyses to identify genes that are specifically associated with stem cell chromosomes, for example genes expressed in model cell lines when they cycle with asymmetric cell kinetics and co-segregate immortal DNA strands. For example, three cell lines of different tissue origin (and one of different species origin) that all divide with asymmetric cell kinetics and the two shown to have immortal DNA strands (Merok et al., 2002) provide rich diversity and complexity from which to identify expressed genes that are common among them. Peptide antibodies can be raised against the predicted proteins of candidate genes. These antibodies can be evaluated for their ability to detect rare cells in known tissue stem cell compartments.

Those of ordinary skill in the art will recognize that a large variety of possible moieties can be coupled to the resultant antibodies or other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., *Imm. Rev.* 62:185-216, 1982; and Vitetta et al., supra).

Preferred linkers are described in the literature. See, for example, Ramalrishnan, S., et al., *Cancer Res.* 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Complexes that form with molecules of the present invention can be detected by appropriate assays, such as the direct binding assay discussed earlier and by other conventional types of immunoassays.

In another preferred embodiment, one could screen a phage display library looking to find antibodies that are specifically associated with immortal strands.

Genetic Methods to Isolate Proteins Specifically Associated with the Immortal Strand In another embodiment of the invention provides for the identification of genes that are required for segregation of the immortal strands to somatic stem cells. For example, mutations may be introduced into cells or cell lines which normally exhibit immortal strand segregation, and the resulting mutants may then be screened to identify cells in which the chromosomes segregate randomly, using genetic methods well known in the art. Mutations may be introduced randomly (using UV or chemical mutagenesis techniques) or introduced into specific genes of interest (e.g. the gene encoding telomerase). Preferably, such genetic screens are carried out on cells from an organism for which genetic techniques are relatively well developed. For example, mice, zebrafish, Drosophila, C elegans, etc. Cell lines include the model cell lines exhibiting conditional asymmetric cell kinetics described above.

In another embodiment of the invention, genes which are involved in the segregation of immortal strands to stem cells can be identified using genetic screens in which wild type proteins are overexpressed.

Methods to Treat Cancer Cells and Aging Tissue

One preferred embodiment of the present invention provides replacing the immortal DNA strand in somatic stem cells by inducing their replication to eliminate the somatic stem cells of age-dependent, environmentally induced and endogenous genomic defects, including those associated with cancer and/or cellular transformation.

Many of the cellular changes that occur in cancer cells and in tissues with advancing age are likely to reflect alterations in the number and function of asymmetrically cycling somatic stem cells. We have discovered that populations of stem cells, including somatic, can retain a set of the same DNA molecules (for at least six generations). As such, much of the decline in stem cell function and, thereby, tissue function results from stable defects in immortal DNA strands in somatic stem cells. These alterations can include stable covalent base modification (e.g., methylation) or poorly repaired forms of oxidative and other chemical damage (production of hypoxanthine and xanthine bases via deamination). Other modifications can include glycosylation, acetylation, phosphorylation, lipidation, and previously unknown modifications. Accumulation of these defects over time eventually lead to declines in stem cell number and function, resulting in cellular transformation, cancer, and the ultimate demise of tissue function and life. Thus, although the ISH may be a key mechanism by which mammalian evolution has limited early death from cancer,[1] it ultimately plays an important function in tissue aging and life span determination. Consequently, occasional replacement of such aged immortal DNA strands in somatic stem cells can serve to rejuvenate both cancerous cells and aged tissues. Done as taught here in a limited and controlled fashion, induced replication and/or replacement of immortal strands helps rid stem cells of age-dependent genomic defects, without greatly increasing the fixation rate of cancer-producing mutations.

Methods to Predict Transplantation Success

The present invention also provides a method for predicting the success of bone marrow transplant engraftment by enumerating the number of stem cells present in the transplanted sample. In this method, a small representative fraction of the bone marrow cell sample is removed prior to transplantation is removed, and the number of stem cells present in that fraction is enumerated. The total number of transplanted stem cells can be estimated from the enumerated fraction. Engraftment success is predicted to increase with the increase in proportion of transplanted stem cells.

EXAMPLES

Example 1

Methods

Cell Culture

Cells were maintained as described.[1,3,15,17,18] The specific lines used were Ind-8 and 1 h-3 for asymmetric kinetics and Con-3 and 1 g-1 for respective control exponential kinetics. [1,3,15,17,18] BrdU was added to cultures at a concentration of 20 µM, either as a 24-hour pulse before the induction of asymmetric cell kinetics, or continuously after induction. For thymidine chase studies, BrdU was added at 5 µM and followed by replacement with BrdU-free medium supplemented with 25 µM thymidine. Asymmetric kinetics by Ind-8 cells were induced at a cell density of $1 \times 10^5$ cells per 75 cm$^2$ flask by switching to growth media containing 72 µM $ZnCl_2$.[3] The number of population division cycles (PDC) was determined in all experiments. PDC is the number of times that an initial population of cycling cells divides. For exponentially dividing cells, PDC=the number of population doublings (PD)=ln $(N_t/N_0)$/ln 2, where $N_0$ and $N_t$ equal the number of cells present in a culture at time 0h and time t, respectively. For asymmetrically dividing cells, PDC was estimated by PDC= $(N_t-N_0)/0.4 N_0$.[3]

CsCl Gradient Density-Shift Analyses

Con-3 and Ind-8 cells were cultured for 24 hours in medium supplemented with 75 µM $ZnCl_2$ to establish asymmetric cell kinetics for Ind-8 cells.[3] BrdU was added to a concentration of 20 µM and culture continued for 15 hours (0.75 GT) and 48 hours (2.4 GT). High molecular weight chromosomal DNA was isolated by phenol:chloroform extraction with proteinase K and RNAase treatment. Ten µg of DNA was centrifuged to equilibrium in a CsCl solution that had an initial refractive index of 1.40. Approximately 0.2-0.4 µg of DNA isolated from Con-3 cells labeled with $^3$H-thymidine was included in gradients as an internal marker for LL-DNA. The DNA content of gradient fractions was quantified by Picogreen dye fluorescence using procedures specified by the supplier (Molecular Probes, Netherlands).

Mitotic Cell Selection

Mitotic cells for flow cytometry and BrdU-pulse analyses were selected by mitotic shake-off into the cultures' own medium after centrifugation to remove debris. Using the same culture medium stabilized the asymmetric cell kinetics during the period of mitotic cell selection. In order to avoid debris, cells from the first two collections were discarded. Collections were then taken every 60 minutes for the next 20 hours. The isolated mitotic cells were maintained on ice until use immediately after the final collection. They were >95% viable by trypan blue analysis.

Flow Cytometry Analysis

Mitotic cells were re-plated in their original culture medium used for mitotic selection and cultured for 5 hours before flow cytometry analysis. Detection of incorporated BrdU was performed with an antibody kit per the instructions of the supplier (#36634K, Pharmingen). BrdU-specific fluorescence was determined with a Becton-Dickinson FACScan flow-cytometer and Cell Quest software.

Chromosome Hoechst Fluorescence Analysis

Mitotic cells for chromosome spread were isolated by a 16-hour treatment with colcemid at a final concentration of 0.1 µg/ml. Mitotic spreads were prepared as previously described.[22] Spreads were stained with Hoechst dye 33258 at a final concentration of 0.5 µg/ml for 5 minutes, and washed 3 times for 5 minutes in PBS just prior to analysis. Fluorescent images were captured using a Nikon Diaphot-TMD microscope and a MTI 3CCD camera, and were analyzed with the Zeiss KS400 software package.

Cytochalasin D Analyses

For BrdU-pulse studies, mitotic cells were isolated as for flow cytometry except the collection medium was supplemented with 2 µM cytochalasin D. After collection on ice, cells were allowed to adhere to chamber slides, cultured for 5 hours, and then fixed for in situ immunofluorescence with a FITC-conjugated anti-BrdU antibody (Pharmingen cat# 36634K) per specifications of the supplier. Fluorescence microscopy was performed with a Zeiss Axioskop 2 phase/epifluorescence microscope and Axiocam digital camera.

For continuous BrdU labeling studies with Zn-dependent Ind-8 cells, asymmetric cell kinetics were induced at a cell density of 500 cells per 1.7 cm² chamber slide by switching to growth media containing 65 µM $ZnCl_2$.[3,11] BrdU was added after asymmetric induction to a concentration of 5 µM. Following a 72-hour growth period, the cultures were arrested by the addition of cytochalasin D (2 µM) for 16 hours. For experiments with temperature-dependent 1 h-3 cells, asymmetric cell kinetics were induced at a density of 7500 cells per 6-cm diameter well by switching to 32.5° C. After 8 hours of growth, BrdU was added to a concentration of 10M. Following a 72-hour growth period, the cultures were arrested by the addition of cytochalasin D (2 µM) for 4 hours. Detection of incorporated BrdU was performed using primary antibody Bu1-75 (Harlan), and a biotinylated secondary antibody (Vector Laboratories) with avidin-fluorescein visualization. Images were captured using a Nikon TE300 microscope, Orca camera, and Openlab software (Improvision). Analysis of captured images was performed with 1D Image Analysis software (Eastman Kodak).

Results

The renewal and maintenance of adult mammalian tissues requires that adult somatic stem cells (SSCs) simultaneously maintain constant number while giving rise to many differentiating tissue cells. Both stochastic and deterministic asymmetric cell kinetics programs have been proposed as the basis of SSC-based tissue cell renewal. Deterministic asymmetric cell kinetics require that SCCs divide continuously to produce one self-replica and a sister cell that is the progenitor of the differentiated cell lineages that make up the tissue of residence.[5-7] Continuous asymmetric kinetics by SSCs over the life of an animal were predicted to put them at high risk for cancer cell initiation due to accumulation of spontaneous mutations that occur during DNA replication. However, observed cancer rates in humans did not meet this expectation.[4]

Based on the observation that human cancer rates did not agree with predictions based on expected mutations rates in adult SSCs, the immortal strand hypothesis (ISH)[4] was proposed to account for how SSCs might avoid altogether mutations that derived from DNA replication errors. FIG. 1 illustrates the salient features of the hypothesis. In the usual view of mitosis by somatic cells, random chromosome assortment occurs as a consequence of independent segregation (FIG. 1B). In contrast, the ISH proposes that a full complement of chromosomes bearing old parental DNA strands (i.e., "immortal DNA strands") continuously co-segregates to long-lived SSCs.

Previously, several groups have reported evidence for the existence of immortal DNA strand co-segregation in adult mammalian tissues in vivo. They based their evidence on detection of cells that appeared either to release incorporated ³H-thymidine more rapidly than would be expected for random chromosome assortment, or to retain the label for extended periods of time.[8-11] Even earlier in vitro studies reported evidence for unequal segregation of labeled mitotic chromosomes in cells from diverse species including cultured murine embryonic fibroblasts and plant meristem cells.[12-13] Chromosome co-segregation mechanisms have also been proposed as a key element of developmental programs responsible for body asymmetry in mammals.[14]

Earlier in vivo studies encountered two main barriers to unambiguous demonstration of immortal DNA strand co-segregation in mammalian cells. First, SSCs were not identifiable; and second, the parental character of immortal DNA strands would preclude labeling them with common base analogues (e.g., bromodeoxyuridine [BrdU] or ³H-thymidine) used for monitoring DNA. We were able to overcome both of these barriers, as well as avoid pharmacokinetics limitations of in vivo labeling studies, by using cultured cells that cycle with deterministic asymmetric cell kinetics.[1-3]

Actual deterministic asymmetric cell kinetics by mammalian cells was first shown with cultured human and murine cells.[1] This was accomplished with cell lines engineered for controlled physiological expression of the p53 tumor suppressor protein.[1,2,15] Subsequently, deterministic asymmetric cell kinetics have been described for stem cell-enriched human bone marrow cells[16] and pre-senescent human and murine fibroblasts.[3] The derivation and cell kinetics properties of the main cell line used for these studies, Ind-8, have been described in detail.[3,17,18] Ind-8 cells are spontaneously immortalized p53-null murine embryo fibroblasts stably transfected with a wild-type p53 cDNA controlled by a metal-responsive gene promoter.

Under routine culture conditions, Ind-8 cells divide with typical exponential kinetics. However, after addition of zinc chloride to the culture medium and the ensuing restoration of p53 protein expression the cells switch to a deterministic asymmetric cell kinetics program. This program is characterized by asymmetric cell divisions that produce two distinct sister cells. One sister is reminiscent of a differentiating transit cell, because it undergoes an immediate viable cell cycle arrest or occasionally divides once to produce two viable arrested cells. The other sister acts like a SSC, undergoing another asymmetric division within one GT period. The generation time (GT) of asymmetrically cycling Ind-8 cells is similar to the GT of the cells when they cycle with exponential kinetics.[3]

Figure 2:
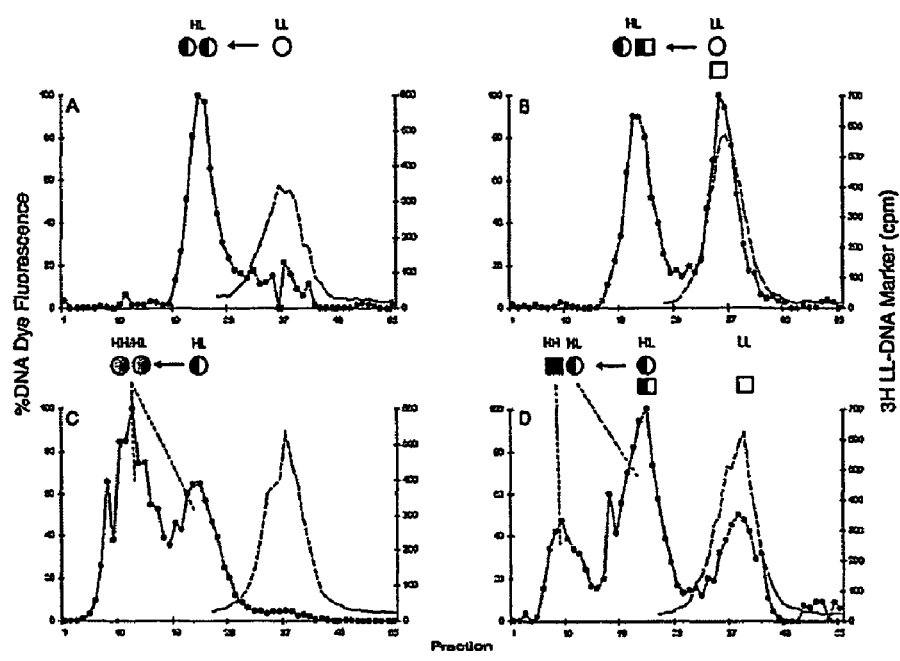
FIGS. 2A-D show bromodeoxyuridine (BrdU) density-shift analysis of DNA replication by cells that cycle with asymmetric cell kinetics. Exponentially cycling control cells (Con-3.

BrdU density-shift analyses in equilibrium CsCl density gradients[19] were performed to confirm that DNA replication remained semi-conservative[20] during asymmetric cell kinetics. The analyses showed DNA species with buoyant densities corresponding to hemi-substitution ("heavy-light", HL) and complete substitution ("heavy-heavy", HH), indicating usual semi-conservative DNA replication (FIGS. 2B and 2D). In addition, the HL-DNA and HH-DNA peaks were discrete (FIG. 2D), denoting continuous synthesis of DNA strands without significant sister chromatid exchange or repair synthesis.

The rates of appearance and relative abundance of BrdU-substituted DNA species from asymmetrically cycling cells reflected their unique cell kinetics. The persistent species with the buoyant density of unsubstituted DNA (FIGS. 2B and 2D; "light-light", LL) is derived from non-cycling sister cells that were produced by asymmetric divisions prior to the addition of BrdU (FIGS. 2B and 2D, open squares). In FIG. 2D, the greater peak area of HL-DNA was due to the next generation of persistent non-dividing sisters (half-filled squares) produced from division of asymmetrically cycling cells that replicated DNA after BrdU addition.

An experimentally testable prediction of the ISH is illustrated by how HH and HL chromosomes distribute between final sister cells in FIGS. 2C and 2D. In FIG. 2C, mitosis by exponentially cycling cells that have undergone two S-phases in BrdU yields two cycling sisters that have, on average, equivalent BrdU content (faded circles) as a result of independent segregation of paired HH·HL sister chromatids. On average, in each sister, 50 percent of the chromosomes are HH, and 50 percent are HL. In contrast, the ISH postulates that an analogous asymmetrically cycling stem-like sister (half-filled circle in FIG. 2D) will co-segregate all HL chromosomes to itself. This maneuver would accomplish retention of unsubstituted immortal DNA strands that were specified by asymmetric cell kinetics mechanisms prior to the addition of BrdU. It follows that the non-dividing sisters would co-segregate only HH chromosomes (solid square in FIG. 2D).

Based on the above discussion, asymmetric sister cells should exhibit a 50 percent difference in nuclear BrdU content (all HH-DNA versus all HL-DNA) if chromosome co-segregation occurred as prescribed by the ISH. To test this prediction, cytochalasin D treatment was used to evaluate the relative BrdU content of sister nuclei. Cytochalasin D is an actin antagonist that permits nuclear division but prevents cytokinesis. It allowed sister nuclei to be trapped in the same cell cytoplasm. The relative differences in the BrdU content of sister nuclei were then quantified by in situ immunofluorescence with anti-BrdU antibodies. These analyses were performed after cells were cultured continuously in BrdU for four population division cycles (PDCs). A PDC is equivalent to one GT, but refers specifically to division by all cells present in an initial cohort of cycling cells (see Methods).

Figure 3:
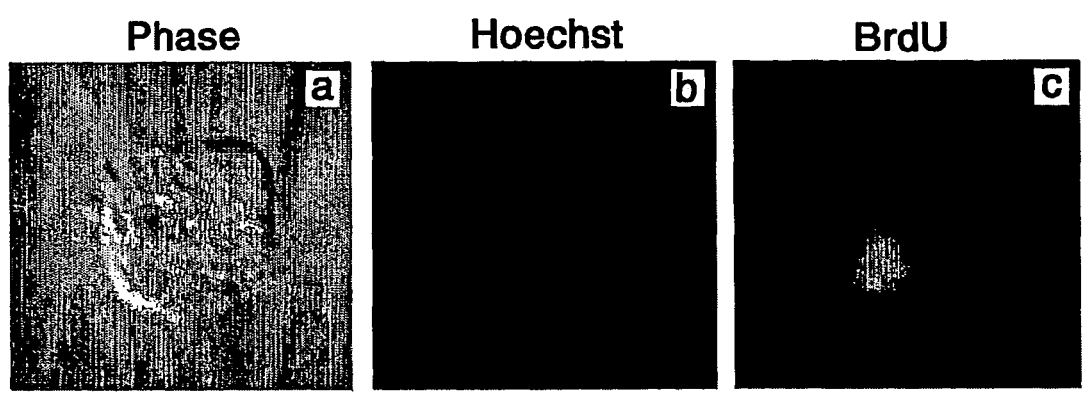
FIGS. 3A-C show analysis of differences in the BrdU content of sister nuclei from asymmetrically cycling cells after continuous labeling. Cells cycling with asymmetric kinetics were cultured continuously in BrdU before treatment with cytochalasin D as described in Methods. The BrdU content of cytochalasin D-arrested cells was determined by in situ immunofluorescence.

Cytochalasin D-arrested binucleated cells from asymmetrically cycling cultures showed unequal BrdU fluorescence (FIG. 3). The difference in BrdU content was confirmed by reciprocal quenching of Hoechst-fluorescence (See FIG. 3, "Hoechst"). The observed mean difference in anti-BrdU fluorescence intensity was 34% (95% CI=24 to 43). This value was less than the ideal difference of 50 percent. However, it differed significantly from the mean value of 15% observed for binucleates for control exponentially cycling cells (mean number of binucleates evaluated =24; p=0.008). Whereas 37% (n=19) of binucleates of asymmetrically cycling cells showed 40% difference in BrdU content (indicative of co-segregation of chromosomes containing unsubstituted immortal DNA strands), all binucleates of exponentially cycling control cells showed <40% difference (n=27). These data yielded an estimated odds ratio of 32 (p<0.05) for greater likelihood to observe a difference in BrdU content in cells cycling with asymmetric cell kinetics.

The continuous BrdU-cytochalasin D analysis was also performed with an independent cell line called 1 h-3. 1 h-3 cells are murine mammary epithelial cells derived with a different p53 gene expression system.[1,2,15] They exhibit the same type of deterministic asymmetric cell kinetics as Ind-8 cells, though not as efficiently.[1]-3 In 1h-3 analyses, 26% (n=31) of binucleates of asymmetrically cycling cells versus 5% (n=44) of binucleates of exponentially cycling cells showed 40% difference in BrdU content (odds ratio=7.3; p<0.05). These results supported the existence of an immortal DNA strand mechanism in cells cycling with asymmetric cell kinetics, independent of their tissue of origin.

Figure 4:
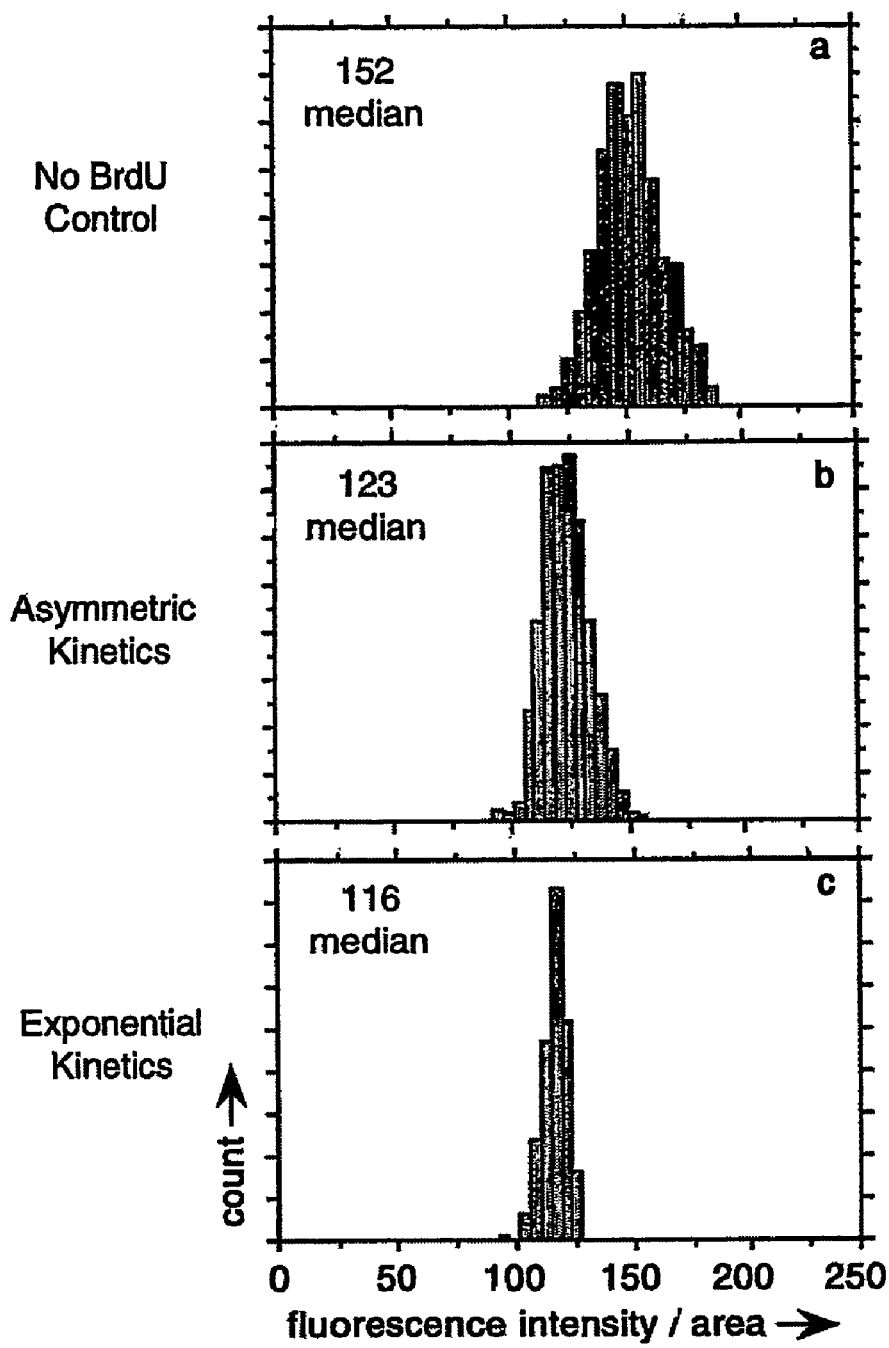
FIGS. 4A-C show mitotic chromosome-spread analysis to detect unsubstituted DNA strands after continuous cycling in the presence of BrdU. Shown are histograms from analyses of the fluorescence intensity per area of individual chromosomes in single-cell mitotic chromosome spreads of the following cells.

Next, analyses with mitotic chromosomes were performed to detect immortal DNA strands without cytochalasin D treatment. Cells were cultured continuously in BrdU-containing medium for 6 PDCs. Labeled cultures were then treated with colcemid to prepare mitotic cells for chromosome spread analyses (see Methods; FIG. 4). To detect chromosomes with unsubstituted DNA strands, mitotic chromosome spreads were stained with the fluorescent DNA dye Hoechst 33258. Incorporated BrdU partially quenches the fluorescence of DNA-bound Hoechst dyes.[21] Mitotic chromosomes that are only hemi-substituted with BrdU exhibit one half the degree of Hoechst-fluorescence quenching observed for fully substituted chromosomes. The fluorescence intensity per pixel area of individual anaphase chromosomes was tabulated in single-cell spreads (see Methods).

Chromosomes from cells cultured without BrdU exhibited the greatest Hoechst-fluorescence (FIG. 4a). Chromosomes from exponentially cycling cells culture in BrdU showed a 24% reduction in median Hoechst-fluorescence (FIG. 4c), indicative of quenching due to full BrdU substitution. Given this difference, the ISH predicted that the chromosomes in asymmetrically dividing mitotic cells should exhibit on average an 18% reduction in median Hoechst-fluorescence (i.e., equivalent to the average of complete reduction [24%] and one half reduction [12%]). The predicted 18% reduction corresponded to a median fluorescence intensity/pixel area of 125. The observed value was 123 (95% CI=122 to 124; FIG. 4b), consistent with retention of chromosomes with unsubstituted immortal DNA strands in cycling stem cell-like sisters during asymmetric cell kinetics.

BrdU-pulse experiments were performed to mark immortal DNA strands and confirm that the chromosomes bearing them co-segregated after mitosis. P53-null control cells and p53-inducible cells were cultured in BrdU for one GT under conditions for exponential kinetics to produce hemi-substituted chromosomes (i.e., HL-DNA). Subsequently, the labeled cells were shifted to BrdU-free medium under conditions that induced asymmetric cell kinetics. After 5 to 6 PDCs, the retention and segregation of BrdU-substituted DNA were evaluated in cycling cells.

In BrdU-pulse experiments, exponentially cycling cells were expected to show a marked reduction in BrdU content due to independent segregation of chromosomes containing BrdU-substituted DNA strands. The random assortment of hemi-substituted chromosomes that results from independent segregation would lead to their geometric dilution among chromosomes with newly synthesized unsubstituted DNA. In contrast, if an immortal strand mechanism operated, asymmetrically cycling stem-like cells were expected to retain their initial BrdU content after many successive divisions. Moreover, chromosomes containing "old" BrdU-substituted strands were predicted to co-segregate to only one sister cell.

Figure 5:
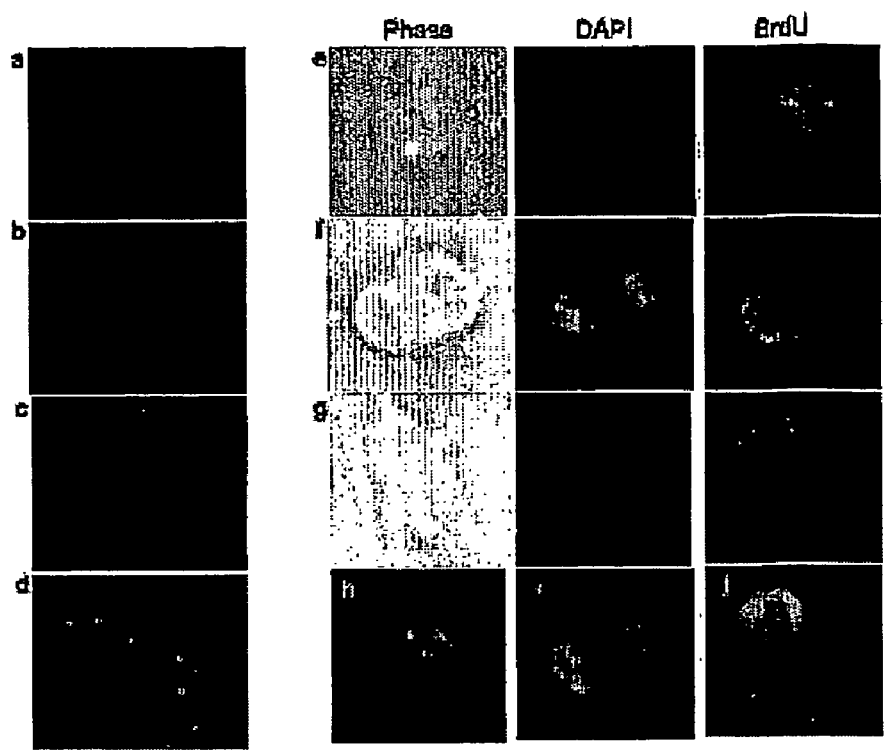
FIGS. 5A-J show microscopic analysis of BrdU-substituted immortal strand co-segregation in cytochalasin D-induced binucleates. Exponentially dividing cells were labeled with BrdU for one generation period and then allowed to cycle in the absence of BrdU either exponentially (FIGS. 5A-5B) or asymmetrically (FIGS. 5C-5J). At 144 hours (approximately 6 population doubling cycles (PDCs)) after the BrdU labeling period, mitotic cells were selected in cytochalasin D-containing medium and returned to culture for 5 hours to allow the formation of binucleated cells. Cells were fixed and examine by in situ immunofluorescence with fluorescent anti-BrdU antibodies. Shown are low magnification fields of nuclear DNA DAPI fluorescence (FIGS. 5A, 5C) and corresponding anti-BrdU fluorescence (FIGS. 5B, 5D) for exponentially (FIGS. 5A, 5B) and asymmetrically (FIGS. 5C, 5D) cycling cells.

To limit the BrdU-pulse analyses to cycling cells, mitotic cells were isolated by mitotic shake-off (see Methods). Collected mitotic cells were returned to culture for 5 hours. During this time, >95% of the cells attached and divided to produce new G1 cells. To visualize segregation patterns of BrdU-containing chromosomes between sister nuclei, isolated mitotic cells were cultured in the presence of cytochalasin D and then analyzed for anti-BrdU immunofluorescence. As predicted, control exponentially cycling cells arrested by cytochalasin D showed very little anti-BrdU fluorescence (FIGS. 5a and 5b). In flow cytometry analyses, new G1 cells produced from control mitotic cells isolated at 5.8 PDC after the BrdU-pulse (without cytochalasin D treatment), showed a uniform marked reduction in BrdU content compared to cells immediately after the BrdU-pulse. Because of the background fluorescence of BrdU-negative cells, a 6.8-fold reduction in median BrdU-fluorescence was observed, instead of the predicted 56-fold (i.e., $2^{5.8}$-fold).

In contrast to the decrease in BrdU content observed for control cells, cytochalasin D-arrested asymmetrically cycling cells exhibited a high degree of anti-BrdU immunofluorescence (FIGS. 5c and 5d). In fact, flow cytometry analysis of G1 cells produced from asymmetrically cycling mitotic cells (in the absence of cytochalasin D treatment) showed two populations of cells. One cell population had a background level of fluorescence, corresponding to the predicted non-dividing sisters that received no chromosomes with BrdU-substituted DNA strands. The other cell population had a BrdU content equivalent to that of cells immediately after the BrdU-pulse (data not shown), corresponding to the predicted cycling stem-like cells that co-segregated chromosomes containing "old" BrdU-substituted DNA strands. In three separate experiments (mean PDC=5.1), the BrdU-retaining population showed a mean dilution factor of 0.82 (95% CI=0.4 to 1.2). This factor was not significantly different than 1.0, the value for complete retention of initial BrdU content In situ anti-BrdU immunofluorescence analyses of cytochalasin D-arrested asymmetrically cycling mitotic cells were consistent with flow cytometry results. Essentially all arrested binucleated cells were positive for BrdU fluorescence (FIG. 5d). Moreover, 22% (n=262) of examined binucleated cells showed nearly complete localization of anti-BrdU immunofluorescence to only one sister nucleus (see examples in FIGS. 5e-j), indicating retention and co-segregation of chromosomes bearing old BrdU-substituted DNA strands as predicted for an immortal strand mechanism. Among binucleated cells with asymmetric BrdU fluorescence, there were many examples of BrdU fluorescence that occurred as a crescent or cap shape that did not fill the entire nuclear DNA space as defined by DAPI fluorescence (for example see FIGS. 5f, g, i, j). Such images may reflect an unusual sequestration of immortal DNA strands in G1 nuclei. These experiments were performed with and without a thymidine chase with similar results (see Methods; data not shown).

Twenty-two percent is a conservative statement of the full extent of immortal strand co-segregation in these experiments. A majority of arrested binucleated cells showed some degree of BrdU fluorescence asymmetry. The fact that not all binucleated cells showed complete co-segregation could reflect intrinsic properties of the cellular mechanisms involved or technical limitations of the experiment. After cytochalasin D treatment in the continuous BrdU-labeling studies (FIG. 3), a larger fraction of binucleated cells showed unequal nuclear BrdU content (i.e., 37% showing a 40% difference). Unlike the BrdU-pulse experiments, the cells in the continuous labeling experiments were examined in situ without isolation by mitotic shake-off. The additional experimental manipulations present in the BrdU-pulse studies might have reversed some cells to symmetric cell kinetics and loss of co-segregation. Finally, given the nearly ideal results obtained in mitotic chromosome analyses (FIG. 4), which did not employ cytochalasin D, it is also possible that cytochalasin D itself compromises the co-segregation mechanism somewhat.

The conclusions for BrdU retention results, quantified by flow cytometry, depended on the occurrence of the prescribed number of serial divisions by cells analyzed at the end of the BrdU-pulse protocol. Therefore, in each experiment, cell number was monitored to determine PDCs (see Methods). The PDC values obtained indicated that the specified number of successive divisions had occurred. Previously, time-lapse studies were used to show that the GT of asymmetrically cycling cells is not significantly different than the GT or exponentially cycling cells.[3] Moreover, the cytochalasin D treatment showed that co-segregation of chromosomes bearing old BrdU-substituted DNA occurred in actively dividing cells.

In the BrdU-pulse studies, there were several possible outcomes for how immortal DNA strands might have been selected upon initiation of asymmetric cell kinetics. If only strands that existed prior to the labeling period were selected, then chromosomes with immortal strands would not be labeled at all. This was not the case. If initial immortal strand selection were a random process, then on average half of the chromosomes with immortal strands would be unsubstituted. The BrdU dilution factor for such a mechanism is predicted to be 2.0, because on average only half of the initially selected immortal strands (in HL chromosomes) would contained BrdU. Finally, if only the most recently synthesized DNA strands were selected, then all chromosomes with immortal strands would contain BrdU, and there would be no dilution. As noted earlier, the experimentally determined dilution factor of 0.82 was not significantly different than 1.0, indicating little or no dilution of BrdU in cycling stem-like cells. However, 0.82 does differ significantly from 2.0 (p<0.031), the factor for random selection. Therefore, our working hypothesis is that immortal DNA strands are not chosen randomly. Instead, upon initiation of the asymmetric cell kinetics program the most recently synthesized DNA strands are selected.

By several independent measures, we provide evidence for an immortal DNA strand mechanism in cells that cycle with asymmetric cell kinetics. The mechanisms by which immortal DNA strands are selected and co-segregated remain to be elucidated. Because p53 is responsible for asymmetric cell kinetics, it may also be involved in immortal strand mechanisms. However, the experiments presented here do not directly address this possibility. The suggestion of clustering of chromosomes bearing BrdU-marked immortal DNA strands in some asymmetrically cycling G1 cells (see FIG. 5) may be a clue to the nature of the immortal strand co-segregation mechanism. However, whether this pattern of chromosome localization is a general feature of the mechanism, in the absence of cytochalasin D treatment, remains to be established.

Two aspects of this study may have relevance to SSCs in vivo. First, the selection of immortal strands at initiation of asymmetric cell kinetics in culture may be related to the establishment of immortal strands in SSCs in late fetal development. The finding that the most recently synthesized DNA strands are selected may be relevant to processes that establish SSCs in newly forming somatic tissues. The same establishment mechanism may recur in adult stem cells under special circumstances (e.g., after exponential divisions for repair of tissue damage). Secondly, immortal strand co-segregation was found to be specific for asymmetric cell kinetics, a property that distinguishes rare SSCs from their abundant differentiating progeny. As such, some factors required for immortal strand selection and co-segregation may uniquely identify adult stem cells.

Some changes that occur in tissues with advancing age are likely to reflect alterations in the number and function of SSCs.[3] The ISH predicts that many adult SSCs retain a set of the same DNA molecules for long periods. Alterations that accumulate in these stable immortal DNA strands over time may compromise SSC function and viability, precipitating a decline in tissue function. Possible alterations include stable covalent base modifications (e.g., methylation) and poorly repaired products of chemical reaction (e.g., oxidative damage and deamination). Thus, although the ISH may be a key mechanism by which mammalian evolution has limited pre-reproductive death from cancer,[4] it may also be an important determinant of tissue aging and life span.

Example 2

Recently, we designed a new assay for detecting asymmetrically cycling cells that co-segregate chromosomes with immortal strands, as depicted in FIG. 6. To perform the assay, cell preparations are first cultured for 16-24 hours with 5-20 µM bromodeoxyuridine (BrdU). For many cycling mammalian cells this time period corresponds to about 1 generation time (i.e., the time required for completion of one cell cycle). During this period, new synthesized DNA strands in stem cells (i.e., new non-immortal strands) are labeled with BrdU. At the end of this period, the BrdU containing medium is replaced with BrdU-free medium supplemented with thymidine (at 5 times the BrdU concentration) to limit further incorporation of BrdU and incubated for 16-24 hours. This period allows a labeled stem cell to make new unlabeled non-immortal DNA strands. Half of the new unlabeled strands hybridize to unlabeled immortal DNA strands (unlabeled chromosomes with immortal strands), and half hybridize to BrdU-labeled strands made one generation earlier (hemi-labeled chromosomes without immortal strands).

In its next cell division, a stem cell with an immortal strand mechanism becomes BrdU-free because it retains all chromosomes that contain an unlabeled immortal DNA strand. The same chromosomes contain a complementary unlabeled strand that was made during the previous thymidine chase period. The same division events produce transit cell daughters that receive all of the remaining BrdU-labeled chromosomes. This diagnostic asymmetric co-segregation event can be detected with the use of cytochalasin D. After 16-24 hours of thyidine chase, cytochalasin D is added to the culture for the next 16-24 hour period. This agent prevents cytokinesis and thereby traps post-mitotic sister nuclei within a single cell. Anti-BrdU immunofluorescence can be used to detect binucleated cells that exhibit one BrdU-negative nucleus and one BrdU-positive nucleus. Such binucleates are diagnostic of immortal strand co-segregation and, therefore, adult stem cells.

Binucleates with asymmetric BrdU segregation can be detected more conveniently and with less expense by using either Hoechst dyes or To Pro 3 dye (Molecular Probes). BrdU quenches Hoechst fluorescence, but enhances the fluorescence of To Pro 3. Therefore, binucleates with asymmetric BrdU segregation will exhibit unequal fluorescence when stained with these dyes. Although the difference in dye fluorescence is less than the difference obtained by anti-BrdU immunofluorescence, the gains in convenience, throughput, and economics out-weight this shortcoming. Of course, the same type of quantitative detection could be achieved by simply culturing cells continuous in BrdU and then staining with either Hoechst or To Pro 3 dyes.

The described functional assay for adult stem cells using anti-BrdU immunofluorescence as the detection method is highly specific. Considering 46 mouse or human chromosomes, the probability of observing a significant occurrence of asymmetric segregation by chance is quite small (in the extreme, $0.5^{46}=1.4\times10^{-14}$). So far, in studies in which immortal strands were labeled (see Merok et al., 2001), asymmetric BrdU segregation has never been observed in cells with transit cell symmetric cell kinetics. The sensitivity of the assay depends on the number of binucleates that can be practically scanned for asymmetric BrdU segregation. We estimate that, by using epifluorescence microscopy instrumentation in general practice, sensitivities between 1 in 100 and 1 in 1000 should be easily attainable for cell suspensions.

The sensitivity and throughput of the assay can be increased by applying more sophisticated quantitative flow cytometry methods. At the end of the assay as described above, a stem cell-derived binucleate is predicted to have the same BrdU content as binucleates derived from transit cells with symmetric kinetics. However, the distribution of BrdU localization in the two types of binucleates will be quite different. Binucleates with asymmetric BrdU segregation will have a much narrower distribution of BrdU. This difference in distribution will be reflected in a narrow peak width of emitted fluorescent light The flow cytometer can detect and quantify such differences as fluorescence peak width, and this information can be used to detect rare cells that differ from the main population of cells with broader peak widths due to the presence of BrdU in both sister nuclei.

The functional assay for adult stem cell detection outline in FIG. 6 can be applied to detection of adult stem cells in situ in tissues. In situ tissue analyses will require more sophisticated tissue preparation and cytological imaging.

Example 3

Adult Stem Cell-Specific Antibodies

Three different strategies will be used to identify adult stem cell-specific proteins. The model cell lines described above provide the advantage of cultured cells that should express some or all such unique proteins. Specific antibodies raised against such proteins are predicted to uniquely recognize adult stem cells in diverse tissues.

The first strategy has the aim of producing antibodies against proteins that associate specifically with immortal DNA strands. Mitotic chromosomes that contain immortal DNA strands will be isolated by fluorescence-activated cell sorting (FACS). The same principles that apply to detection of immortal DNA strands in situ can be applied to their isolation by FACS. Hybridoma cell lines will be derived against proteins extracted from the chromosomes and screened for the production of monoclonal antibodies with specific reactivity against immortal strand-containing chromosomes.

The second strategy uses 2-dimensional gel analyses to look for proteins that are only extracted from immortal strand-containing chromosomes. The identities of such proteins will be established by micro-sequencing and protein bioinformatics. Anti-peptide antibodies will be raised against proteins identified by this second method and evaluated for specific reactivity against immortal strand-containing chromosomes.

For the third strategy, gene micro-array analyses will be used to identify genes, ideally of presently unknown function, that are specifically expressed in model cell lines when they cycle with asymmetric cell kinetics and co-segregate immortal DNA strands. The three cell lines of different tissue origin (and one of different species origin) that all divide with asymmetric cell kinetics and the two shown to have immortal DNA strands (Merok et al., 2002) provide rich diversity and complexity from which to identify expressed genes that are common among them. Peptide antibodies will be raised against the predicted proteins of candidate genes. These antibodies (and those from the chromosome analyses described above) will be evaluated for their ability to detect rare cells in known tissue stem cell compartments.

REFERENCES

1. Sherley, J. L., Stadler, P. B. & Johnson, D. R. Expression of the wild-type p53 antioncogene induces guanine nucleotide-dependent stem cell division kinetics. *Proc Natl Acad Sci USA* 92, 136-140. (1995).
2. Sherley, J. L., Stadler, P. B. & Stadler, J. S. A quantitative method for the analysis of mammalian cell proliferation in culture in terms of dividing and non-dividing cells. *Cell Prolif* 28, 137-144. (1995).
3. Rambhatla, L. et al. Cellular senescence: ex vivo p53-dependent asymmetric cell kinetics. *Journal of Biomedicine and Biotechnology* 1, 28-37. (2001).
4. Cairns, J. Mutation selection and the natural history of cancer. *Nature* 255, 197-200. (1975).
5. Lajtha, L. G. Stem cell concepts. *Differentiation* 14, 23-34 (1979).
6. Potten, C. S. Cell cycles in cell hierarchies. *Int J Radiat Biol Relat Stud Phys Chem Med* 49, 257-278. (1986).
7. Herrero-Jimenez, P. et al. Mutation, cell kinetics, and subpopulations at risk for colon cancer in the United States. *Mutat Res* 400, 553-578. (1998).
8. Potten, C. S., Hume, W. J., Reid, P. & Cairns, J. The segregation of DNA in epithelial stem cells. *Cell* 15, 899-906. (1978).
9. Bickenbach, J. R & Mackenzie, I. C. Identification and localization of label-retaining cells in hamster epithelia *J Invest Dermatol* 82, 618-622. (1984).
10. Bickenbach, J. R. & Holbrook, K. A. Label-retaining cells in human embryonic and fetal epidermis. *J Invest Dermatol* 88, 42-46. (1987).
11. Morris, R. J. & Potten, C. S. Highly persistent label-retaining cells in the hair follicles of mice and their fate following induction of anagen. *J Invest Dermatol* 112, 470-475. (1999).
12. Lark, K. G., Consigli, R. A. & Minocha, H. C. Segregation of sister chromatids in mammalian cells. *Science* 154, 1202-1205. (1966).
13. Lark, K. G. Nonrandom segregation of sister chromatids in *Vicia faba* and *Triticum* boeoticum. *Proc Natl Acad Sci USA* 58, 352-359. (1967).
14. Klar, A. J. S. Genetic models for handedness, brain lateralization, schizophrenia, and manic-depression. *Schizophrenia Res.* 39, 207-218. (1999).
15. Sherley, J. L. Guanine nucleotide biosynthesis is regulated by the cellular p53 concentration. *J Biol Chem* 266, 24815-24828. (1991).
16. Huang, S., Law, P., Francis, K., Palsson, B. O. & Ho, A. D. Symmetry of initial cell divisions among primitive hematopoietic progenitors is independent of ontogenic age and regulatory molecules. *Blood* 94, 2595-2604. (1999).
17. Liu, Y., Bohn, S. A. & Sherley, J. L. Inosine-5'-monophosphate dehydrogenase is a rate-determining factor for p53-dependent growth regulation. *Mol Biol Cell* 9, 15-28. (1998).
18. Liu, Y. et al. Comparison of bax, waf1, and IMP dehydrogenase regulation in response to wild-type p53 expression under normal growth conditions. *J Cell Physiol* 177, 364-376. (1998).
19. Meselson, M., Stahl, F., and Vinograd, J. Equilibrium sedimentation of macromolecules in density gradients. *Proc. Natl. Acad. Sci. USA* 43, 581-588 (1957).
20. Meselson, M. and Stahl, F. W. The replication of DNA in *Escherichia coli*. *Proc. Natl. Acad. Sci. USA* 44, 671-682 (1958).
21. Latt, S. A., Stetten, G., Juergens, L. A., Willard, H. F. & Scher, C. D. Recent developments in the detection of deoxyribonucleic acid synthesis by 33258 Hoechst fluorescence. *J Histochem Cytochem* 23, 493-505. (1975).
22. Paul, J. R. *Cell and Tissue Culture* (Williams and Wilkins, Co., Baltimore, Md., 1960).

All references described herein are incorporated herein by reference.

We claim:

1. A method for identifying asymmetrically dividing neuronal or liver cells which comprises
    a) labeling cells undergoing cell cycle division by exposing said cells to a detectable nucleotide analogue for the duration of one cell cycle;
    b) removing the nucleotide analogue and growing the cells in the absence of said analogue for the duration of another cell cycle;
    c) treating the cells to allow the identification and comparison of two sister nuclei which share a common parental nucleus; and
    d) identifying those unlabeled nuclei which contain only unlabeled chromosomes which have not incorporated said detectable nucleotide analogue, but which have a labeled sister nucleus which does contain labeled chromosomes; wherein the unlabeled chromosomes in said unlabeled nuclei are chromosomes that have separated asymmetrically; and wherein the cells with an unlabeled nucleus and a labeled sister nucleus are asymmetrically dividing neuronal or liver cells.

2. The method of claim 1, further comprising isolating the identified asymmetrically dividing neuronal or liver cells.

3. The method of claim 1, wherein the detectable nucleotide analogue is selected from the group consisting of 5-bromo-deoxyuridine (BrdU), $^3$H-thymidine, halogenated nucleotide analogues, and iodo-uridine.

4. The method of claim 3, wherein the detectable nucleotide analogue is BrdU.

5. The method of claim 1, wherein the treatment of cells which allows the identification and comparison of two sister nuclei which share a common parental nucleus is selected from the group consisting of cytochalasin D, colcemid, chochicine, mitotic shake-off, nocodazole, cell synchronization, expression of specific mitotic arrest genes, and repression of specific mitotic promoting genes.

6. The method of claim 5, wherein the treatment is cytochalasin D.

7. The method of claim 1, further comprising the step of isolating mitotic cells prior to exposing cells to a detectable nucleotide analogue.

8. The method of claim 7, wherein said mitotic cells are isolated by mitotic shake-off, wherein mitotic cells are isolated every hour by shaking cell cultures to loosen cells undergoing mitosis and collecting the culture medium.

9. The method of claim 8, wherein the mitotic cells from the first two collections are discarded.

10. The method of claim 7, where the mitotic cells are maintained at 4° C. prior to exposing cells to the nucleotide analogue.

11. The method of claim 1, wherein said stem cell chromosomes contain alterations selected from the group consisting of modifications and structural conformations.

12. The method of claim 11, wherein the modification is selected from the group consisting of methylation, deamination, glycosylation, acetylation, phosphorylation, lipidation, and previously unknown modifications.

13. The method of claim 11, wherein the structural conformation alteration is selected from the group consisting of a region of single-stranded DNA and a region of double-stranded DNA.

14. The method of claim 13, wherein the structural conformation alteration is a region of single-stranded DNA.

15. The method of claim 13, wherein the structural conformation alteration is a region of double-stranded DNA.

16. The method of claim 1, wherein the neuronal or liver cells are somatic stem cells undergoing asymmetrical kinetics.

* * * * *